(12) United States Patent
Henderson

(10) Patent No.: US 7,153,503 B1
(45) Date of Patent: Dec. 26, 2006

(54) COMPREHENSIVE DIETARY SUPPLEMENT

(76) Inventor: Janeel Henderson, 15 S. Country La., Fruit Heights, UT (US) 84037

( * ) Notice: Subject to any disclaimer, the term of this patent is extended or adjusted under 35 U.S.C. 154(b) by 0 days.

(21) Appl. No.: 10/344,865

(22) PCT Filed: Dec. 18, 1999

(86) PCT No.: PCT/US99/30340

§ 371 (c)(1),
(2), (4) Date: Apr. 21, 2003

(87) PCT Pub. No.: WO00/37087

PCT Pub. Date: Jun. 29, 2000

Related U.S. Application Data

(60) Provisional application No. 60/113,150, filed on Dec. 19, 1998.

(51) Int. Cl.
*A61K 38/43* (2006.01)
(52) U.S. Cl. .................................. 424/94.01
(58) Field of Classification Search ............... None
See application file for complete search history.

(56) References Cited

U.S. PATENT DOCUMENTS

| | | |
|---|---|---|
| 4,599,152 A | 7/1986 | Ashmead |
| 4,830,716 A | 5/1989 | Ashmead |
| 4,863,898 A | 9/1989 | Ashmead et al. |
| 5,292,538 A | 3/1994 | Paul et al. |
| 5,332,579 A | 7/1994 | Umbdenstock |
| 5,405,613 A | 4/1995 | Rowland |
| 5,569,458 A | 10/1996 | Greenberg |
| 5,888,553 A | 3/1999 | Grant et al. |
| 5,895,652 A * | 4/1999 | Giampapa .............. 424/195.17 |
| 5,904,924 A | 5/1999 | Gaynor |
| 5,948,443 A | 9/1999 | Riley |
| 5,994,295 A | 11/1999 | Khoo |

FOREIGN PATENT DOCUMENTS

| EP | 659402 A2 * | 6/1995 |
|---|---|---|
| WO | PCT/US92/09587 | 11/1992 |

OTHER PUBLICATIONS

Siberian ginseng (http://www.vitaminuk.com/pages/asticles/siberianginseng.htm, Feb. 1, 2006.*

* cited by examiner

*Primary Examiner*—Ralph Gitomer
*Assistant Examiner*—Kailash C. Srivastava
(74) *Attorney, Agent, or Firm*—Thorpe North & Western, LLP

(57) ABSTRACT

A comprehensive dietary supplement of bioavailable minerals, vitamins, phytonutrients, herbs, antioxidants, and enzymes for ameliorating the effects of stress and premature aging, for enhancing natural cellular rejuvenation and regeneration, and for fortifying the immune system of a warm-blooded animal or human, comprises, in parts by weight (a) about $100-500 \times 10^{-3}$ of a blend of vitamins, (b) about $200-800 \times 10^{-3}$ of blend of minerals wherein said minerals are present as amino acid chelates formed from an amino acid ligand and said minerals, wherein the mole ratio of amino acid ligand to mineral in said chelate is at least 1:1, (c) about $250-750 \times 10^{-3}$ of a blend of phytonutrients, (d) about $50-500 \times 10^{-3}$ of a blend of herbs, and (e) about $30-500 \times 10^{-3}$ of a blend of enzymes.

24 Claims, No Drawings

COMPREHENSIVE DIETARY SUPPLEMENT

RELATED APPLICATIONS

This application is a 35 U.S.C. 371 nationalization of PCT/US 99/30340 filed 18 Dec. 1999 which claims the benefit of U.S. Provisional Application Ser. No. 60/113,150 filed 19 Dec. 1998.

BACKGROUND OF THE INVENTION

This invention relates to dietary supplements. More particularly, the invention relates to a comprehensive dietary supplement comprising vitamins, bioavailable minerals in the form of amino acid chelates, phytonutrients, enzymes, herbs and antioxidants.

Since the publication of *The Origin of Species* by Charles Darwin in 1859, the extraordinary advances made in our knowledge of the molecular basis of health maintenance have brought an intellectual revolution in biology. Many fields of science have brought penetrating new insights into some of the most fundamental problems in cell structure and function and have led to a more comprehensive and more widely applicable framework for the science of biochemistry.

Cells function as chemical engines because they posses enzymes, catalysts capable of significantly increasing the rate of certain chemical reactions. Well over one thousand different enzyme systems have been identified and/or characterized. Enzymes are highly specialized proteins. Each type of enzyme can catalyze only one specific type of chemical reaction.

Enzymes have evolved to far exceed man-made catalysts in their reaction specificity, catalytic efficiency, and their capacity to operate under mild conditions of temperature and hydrogen ion concentration. They can catalyze in milliseconds, complex sequences of reactions that would require days, weeks, or months of work in the chemical laboratory.

Part of the evolutionary process has been the rendering of optimal functionality of enzymes by association with certain physiological substances. Optimal adaptation of enzyme systems was and still is a function of raw materials that were present during evolutionary change. These raw materials, which are known to enhance the biological activity of enzymes, are derived from a combination of earth metals and metabolic by-products of living things.

Vitamins are a group of organic substances, present in minute amount in natural food stuffs, that are essential to normal metabolism. Inasmuch as the human body does not synthesize many "essential compounds," such as specific vitamins and minerals, these can be obtained from only two sources: food and supplements. The primary source of all nutrients is food. However, ample evidence documents that majority of the human population stratified by agen, gender, socioeconomic status, life styles and other variables, cannot meet the "Recommended Dietary Allowances" of foods containing these essential compounds and elements. Thus vitamin and mineral supplementation has become a recognized method of meeting accepted medical and public health nutrient standards.

Antioxidants are known to be advantageous in the diet for providing a protective effect against free radicals and oxidative damage that can occur in the gastrointestinal system as well as other various target tissues and organs including the liver, lungs, kidneys, and blood. It is believed that the free-radical effects on cells and tissues can be modified by antioxidants and so reduce cellular damage. Indeed, diets rich in antioxidants have been associated with longevity and with a decreased risk of many types of cancer.

Currently, many types of dietary vitamins and mineral formulas are in common use. See, for example, U.S. Pat. Nos. 5,292,538; 5,888,553; 5,904,924; and 5,569,458. However, they possess certain inherent deficiencies which detract from their overall utility. First of all, the prior art formulas typically do not contain appropriate bioavailable forms of minerals for intestinal absorption and transport for utilization as electrolytes, enzyme co-factors, and the like. Additionally, though many prior art formulas contain vitamins and minerals, they are not ratio proportioned so as to mimic the optimal levels found in healthy and active cells. Furthermore, most of these formulas do not contain enzymes to enhance the body's digestion and absorption of nutrients. In addition, no prior art formula contains a blend of phytonutrients comprising one or more members selected from grape seed extract, broccoli, cabbage, carrot, apple pectin, fructo-oligosaccharide(FOS) and Atlantic Kelp. Furthermore, most prior art formulas do not contain a blend of herbs selected from the group consisting of gingko biloba, garlic, Cayenne pepper, green tea extract, Gotu Kola extract, Tumeric extract, Siberian Ginseng, and Aloe vera extract, which provide synergistic nutrients in proper ratios to be used to the fullest benefit of the user.

In view of the foregoing, it will be appreciated that providing a dietary supplement that supplies a sufficient and optimal balance of minerals and vitamins as cofactors for enzymes, enzymes for aiding in digestion and utilization of foods especially proteins and dairy products, antioxidants for neutralizing free radicals in the body, and blends of phytonutrients and herbs would be advantageous to provide synergistic nutritional effects. Importantly, the inclusion of sufficient levels of minerals in the proper ratio and in bioavailable forms along with a blend of phytonutrients, enzymes and herbs, to provide for balanced and synergistic nutrients without causing any undesirable side effects would be of great advantage and a significant advancement in the art.

BRIEF SUMMARY OF THE INVENTION

It is an object of the present invention to provide a dietary supplement comprising bioavailable minerals, coenzymes, enzymes, and antioxidants.

It is another object of the invention to provide a comprehensive dietary supplement comprising vitamins, amino acid-chelated minerals, phytonutrients, herbs, antioxidants, and enzymes.

It is also an object of the invention to provide a dietary supplement for ameliorating the effects of stress and premature aging.

It is still another object of the invention to provide a dietary supplement for establishing an environment in the body for natural cellular rejuvenation and regeneration.

It is yet another object of the invention to provide a dietary supplement for fortifying the immune system.

These and other objects can be achieved by providing a comprehensive dietary supplement comprising in parts by weight (a) about $100–500 \times 10^{-3}$ of a blend of vitamins, (b) about $200–800 \times 10^{-3}$ of a blend of minerals present as amino acid chelates formed from one or more amino acid ligands and said minerals, wherein the mole ratio of amino acid ligand to mineral in said chelate is at least 1:1, (c) about $250–750 \times 10^{-3}$ of a blend of phytonutrients, (d) about $50–500 \times 10^{-3}$ of a blend of herbs, (e) about $30–500 \times 10^{-3}$ of a blend of enzymes, and (f) an effective amount of a blend antioxidants. The antioxidants are primarily contained in the vitamin and mineral blends referenced above and are selected from the group consisting of about $10\text{--}500 \times 10^{-3}$ parts by weight of vitamin C, about 1–500 international units of vitamin E, about $0\text{--}10{,}000 \times 10^{-6}$ parts by weight of β-carotene, about $1\text{--}75 \times 10^{-6}$ parts by weight of selenium. However, additionally, the formulation can contain, as antioxidants about $0\text{--}500 \times 10^{-3}$ parts by weight of N-acetyl cysteine, about $0\text{--}200 \times 10^{-6}$ parts by weight of lipoic acid, and mixtures thereof. Optionally, the comprehensive dietary supplement also contains about $0\text{--}550 \times 10^{-3}$ parts by weight of certain lipotropic agents and about $0\text{--}50 \times 10^{-3}$ parts by weight of branched amino acids.

DETAILED DESCRIPTION

Before the present dietary supplement is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a dietary supplement containing "a vitamin" includes a mixture of two or more vitamins, reference to "an antioxidant" includes reference to one or more of such antioxidants, and reference to "an enzyme" includes reference to a mixture of two or more enzymes.

In describing and claiming the present invention, the following terminology will be used in accordance with the definitions set out herein.

"Carrier" means any suitable carrier and may be caloric or non-caloric. Inert carriers such as those used as tableting aids or lubricants, e.g. magnesium stearate, carbohydrates (sugar or starch) or proteins may be utilized.

"Protein carrier" or "protein based carrier" means a protein or hydrolyzed protein derived from either animal or plant sources and may also contain other additives such as carbohydrates, flavoring agents, vitamins, minerals, phytonutrients, enzymes, herbs and other additives that do not detract from the beneficial effect of the supplement and do not cause undesirable side effects.

"Effective amount" shall mean the amount each nutrient that is required to bring about the desired nutritional and/or therapeutical response and may vary considerably according to the individual, his or her genetic makeup, size, weight and environment. It may be difficult to categorically state that "x" grams, milligrams, micrograms, etc. of any given nutrient is sufficient and may have to be empirically determined. The ranges contained herein are adequate to allow one skilled in the art to determine the formulation to be prepared for each individual.

The following discussion is included for purpose of describing the present invention and illustrating a preferred embodiment thereof and is not intended to be limiting in scope of the specific formulas or composition disclosed. As previously stated, the present invention provides a comprehensive dietary supplement comprising in parts by weight (a) about $100\text{--}500 \times 10^{-3}$ of a blend of vitamins, (b) about $200\text{--}800 \times 10^{-3}$ of a blend of minerals present as amino acid chelates formed from an amino acid ligand and said minerals, wherein the mole ratio of amino acid ligand to mineral in said chelate is at least 1:1, (c) about $250\text{--}750 \times 10^{-3}$ of a blend of phytonutrients, (d) about $50\text{--}500 \times 10^{-3}$ of a blend of herbs, (e) about $30\text{--}500 \times 10^{-3}$ of a blend of enzymes, and (f) an effective amount of a blend antioxidants. As noted above, the antioxidants are primarily contained in the vitamin and mineral blends and are selected from the group consisting of about $10\text{--}500 \times 10^{-3}$ parts by weight of vitamin C, about 1–500 international units of vitamin E, about $0\text{--}10{,}000 \times 10^{-6}$ parts by weight of β-carotene, about $1\text{--}75 \times^{-6}$ parts by weight of selenium. However, additionally, the formulation can contain, as antioxidants about $0\text{--}500 \times 10^{-3}$ parts by weight of N-acetyl cysteine, about $0\text{--}200 \times 10^{-6}$ parts by weight of lipoic acid, and mixtures thereof.

The above ingredients have been stated in terms of parts by weight in order to show the relative proportion of one ingredient to another. The "unit dosage" amount of each ingredient may be obtained by converting each part by weight (discounting the $10^{-3}$ designation) into a millgrain (mg) and also converting each part by weight (discounting the $10^{-6}$ designation) into a microgram (mcg) in the metric system. The concentration of each ingredient will obviously be a function of how many ingredients are in a unit dosage form. It is generally desired that each unit dosage be in the range of between about 5 to 50 grams. Hence, any difference between the sum of the unit dosage weights of the ingredients named and the overall unit dosage will preferably be made up of a carrier. In the alternative, if the unit dosage is too great to be administered at one time, it may be apportioned into multiple doses and be administered over a given period of time. A unit dosage may or may not be a daily dosage.

Bioavailable forms of magnesium, calcium, and other minerals, such as iron, zinc, selenium, copper, manganese, and chromium, which are properly used in facilitating enzyme efficiency, are those made by chelating or complexing the mineral with an amino acid or peptide ligand, wherein the ligand to mineral ratio is at least 1:1 and is preferably 2:1 or higher and wherein the molecular weight of the amino acid chelate formed is not greater than about 1500 daltons and preferably does not exceed about 1000 daltons. Optionally, the amino acid or peptide chelated minerals are pharmaceutical grade in purity. Such amino acid chelates are stable and are generally taught in the prior art to be absorbed intact through the intestinal tract via an active dipeptide transport system. It has not been previously shown that, when properly administered, such chelates can cooperate with vitamins, phytonutrients, herbs, antioxidants, and enzymes, to synergistically effect a comprehensive dietary supplement. Such amino acid chelates have a stability constant of between about $10^6$ and $10^{16}$. A more detailed description of such chelates and the method by which they are absorbed through the intestine is documented in Ashmead et al., U.S. Pat. No. 4,863,898, issued Sep. 5, 1989, and also in Ashmead et al., *Intestinal Absorption of Metal Ions and Chelates*, published by Charles C. Thomas, Springfield, Ill., 1985. Boron, as a metalloid, may be present more in the form of a complex or salt than as an actual chelate.

This invention, however, is not directed to metal uptake into tissues or metal transport across the intestine for absorption in the blood. Therefore, although amino acid chelates and some of the uses to which they are applicable are documented in the art, there is no teaching that proper formulations and administration of such chelates can affect comprehensive dietary supplementation when co-administered with properly formulated vitamins, phytonutrients, herbs, antioxidants, and enzymes as defined herein.

To clarify what is meant by the term "amino acid chelate", the American Association of Feed Control Officials has issued the following official definition: "amino acid chelate—a metal ion from a soluble salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800." It is also now well documented that amino acid chelates can be prepared from metal ions that do not come from soluble salts. Ashmead, U.S. Pat. No. 4,599,152, and Ashmead, U.S. Pat. No. 4,830,716, both disclose methods of preparing pure pharmaceutical grade amino acid chelates using metal sources other than soluble metal salts. It is not essential to the present invention the manner in which the amino acid chelates are made, provided they meet the criteria stated above. However, it is preferable that pharmaceutical grade chelates be used in the present invention in order to minimize the presence of unwanted impurities, such as sulfate ions, excess chloride, and the like.

As referenced above, various studies have found that minerals that are chelated or complexed by amino acids, or combinations of amino acids and vitamin acid ligands, (e.g. glycinates, arginates, and nicotinate glycinates) are bioavailable forms that render the minerals more readily absorbed by virtue of the fact that transport across the intestinal mucosa and into the portal circulation is accomplished by an amino acid transport mechanism and not by traditional mineral acid transport mechanisms. Once in the blood, the amino acid chelates do not bind directly to serum proteins, but are transported directly to target tissues in the chelated form. Thereafter, the mineral is released intracelluarly from the chelate. Importantly, this direct transport results in greatly improved bioavailability of the minerals to the end organs and/or cells and works independent of either mineral saturated or reduced concentrations of serum proteins. Additionally, unlike most conventional mineral salts that are commercially available, amino acid chelates do not cause changes in bowel habits after oral administration. This is in contrast to notable examples of conventional iron salts such as iron sulfate, which may cause constipation, and magnesium citrate which commonly causes loose stools or diarrhea.

While the amino acid or peptide ligands used in formulating the amino acid chelates are in themselves important nutrients, in the present invention, they may or may not be present in amounts sufficient to act as a protein calorie source. In any event, they are important factors in furthering the cause of dietary supplementation. Amino acid chelates of copper, zinc, iron, manganese, and optionally selenium are known to reduce free radical cellular oxidative stress by strengthening and maintaining the activities of enzymes known to remove harmful superoxides, peroxides, and hydroxides. WO 93/10777. These enzymes include, but are not limited to, superoxide dismutase, catalase, and glutathione peroxidase. The superoxide radical is formed during various metabolic processes, many of which are considered normal. Liver cells, muscle cells, leukocytes, erythrocytes, aerobic bacteria, and any cell that undergoes oxidative cellular metabolism, all form superoxide radicals during normal metabolic processes. These oxygen radicals are converted to hydrogen peroxide by CuZn-superoxide dismutase in the cells. In a properly functioning system the hydrogen peroxide is then converted to oxygen and water by catalase. If the hydrogen peroxide and the superoxide radical are allowed to combine, the more reactive and destructive hydroxide radical is formed. When the formation of one or more of the superoxide, hydrogen peroxide, or hydroxide radicals becomes uncontrolled or the organism loses the ability to regulate these reactions, changes in cellular physiology result that become detrimental to the individual cells, organ systems, or the entire host or animal. Some of these changes include generalized tissue destruction, lameness and joint destruction, DNA miscoding or degradation, lipid peroxidation, altered immune function, and inactivation of important cellular enzymes.

The primary activated superoxide dismutase (SOD) in animals is CuZnSOD. This metalloenzyme undergoes a reduction-oxidation exchange with the superoxide radical with the net result of dismutation of the superoxide radical to hydrogen peroxide and oxygen. As noted, the metals for this activity are copper and zinc. Other forms of SOD, i.e. MnSOD and FeSOD, are also known, but occur primarily in bacteria and mitochondria. Without the presence of copper, the eukaryotic cytocell SOD enzyme is virtually inactive. The activity of the CuZnSOD enzyme can be suppressed by the rapid accumulation of hydrogen peroxide. Therefore, it is essential that other enzymes that deplete hydrogen peroxide be functional within the cells to maintain SOD activity.

Catalase is a large molecular weight enzyme that contains four heme groups per molecule. Catalase is the primary enzyme necessary for the breakdown of hydrogen peroxide in the cell to oxygen and water and is found in all cells of the body that utilize oxygen.

Glutathione peroxidase (GSH-Px) has a selenium dependent form that contains four moles of selenium per mole of enzyme. The oxidative role of this enzyme is similar to catalase in that it converts hydrogen peroxide to water and oxygen. Whenever catalase or glutathione peroxidase activity is impaired there can be a toxic build-up of peroxides. This, in turn, can lead to a build-up of the hydroxide radical. The non-selenium glutathione peroxidase (GSH-P) plays a role in controlling lipid peroxidation. The primary form of glutathione peroxide in red blood cells is the selenium dependent form, which maintains a linear relationship to selenium status within the animal and has been used to indicate whether or not a selenium deficiency exists.

From the above, it is evident that proper metabolic functioning of minerals such as copper, zinc, iron, and manganese in addition to or independent of selenium play an important role in maintaining the function of oxidative enzymes that relate to oxidative bursts in neutrophils and macrophages, and in controlling or alleviating free radical cellular oxidative toxicity. Over a period of time, deficiency of these minerals in the body in bioavailable forms results in a compromised enzyme deactivation system, and the accumulation of free radicals within oxygen consuming cells leading to free radical toxicity. It would therefore be beneficial to provide these essential minerals in a bioavailable form wherein such minerals would be readily absorbed and utilized for the repair and maintenance of the appropriate enzyme systems.

Therefore, a comprehensive dietary supplement, according to the present invention, comprises bioavailable minerals in proportions that enhance endogenous enzyme activity and promote maintenance of good health. The mineral blend utilized in the present invention will contain amino acid chelated calcium, iron, magnesium, zinc, selenium, copper, manganese and chromium in the parts by weight ranges indicated in the following table and will also preferably contain one or more minerals selected from the group consisting of boron and vanadium. Optionally, molybdenum and potassium will also be present. Preferred ranges of these minerals are:

| BIOAVAILABLE MINERALS | RANGES IN PARTS BY WEIGHT |
|---|---|
| Calcium | $50-500 \times 10^{-3}$ |
| Iron | $1-50 \times 10^{-3}$ |
| Magnesium | $50-500 \times 10^{-3}$ |
| Zinc | $1-25 \times 10^{-3}$ |
| Selenium | $1-75 \times 10^{-6}$ |
| Copper | $0.1-2 \times 10^{-3}$ |
| Manganese | $0.1-10 \times 10^{-3}$ |
| Chromium | $25-300 \times 10^{-6}$ |
| Boron | $0.025-25 \times 10^{-3}$ |
| Vanadium | $0.1-10 \times 10^{-6}$ |
| Molybdenum | $0-100 \times 10^{-6}$ |
| Potassium | $0-500 \times 10^{-3}$ |

The composition will contain about $200-800 \times 10^{-3}$ parts by weight of a mineral blend containing the above minerals, as amino acid chelates, in the relative amounts and/or proportions given. As noted above, selenium also provides an antioxidant function.

In addition to minerals, vitamins are essential for maintaining good health. Vitamins are organic compounds that are required for the normal growth and maintenance of life in animals including man, who, as a rule, are unable to synthesize these compounds in the body. Vitamins are essential for the transformation of energy and for the regulation of the metabolism. They or their precursors are found in plants, and, so far as is known, have specific metabolic functions to perform in plant cells. Plant tissues are the sources for the animal kingdom of these protective nutritional factors. It is essential that the food of man and animals contain small amounts of these organic substances. If any one of at least 12 vitamins is lacking in the diet, there occurs eventually a breakdown of the normal metabolic processes that results in a reduced rate or complete lack of growth in children, and in symptoms of malnutrition that are classified as deficiency diseases.

Vitamins are unlike each other in their chemical composition and their function. They are alike, however, in that they cannot be synthesized at all or at least not at an adequate rate in the tissues of all animals. Their functions fall into two categories, the maintenance of normal structure and of normal metabolic functions. For example, Vitamin A is essential for the maintenance of normal epithelial tissue. Vitamin D functions in the absorption of normal bone salts for the formation and growth of a sound bony structure. Certain vitamins of the water-soluble group, among them thiamine, riboflavin, pantothenic acid, and niacin, are known to be essential constituents of the respiratory enzymes that are required in the utilization of energy from oxidative catabolism of sugars and fats. It is convenient to categorize vitamins into water-soluble and fat-soluble groups. Vitamins A, D, E, and K fall into the fat-soluble group. Vitamin C and the B group of vitamins are water soluble. J. W. Boehne & M. R. Spivey Fox, Vitamins and Other Nutrients, in Remington's Pharmaceutical Sciences 935–970 (15th ed., 1975).

Thus, it is advantageous to add sufficient vitamins in a balanced ratio to a comprehensive dietary supplement. Preferred amounts of such vitamins are described below.

| VITAMINS | RANGES IN PARTS BY WEIGHT OR IU |
|---|---|
| Vitamin A (including β-Carotene) | 500–20,000 IU |
| Vitamin C | $10-500 \times 10^{-3}$ |
| Vitamin D | 25–1000 IU |
| Vitamin E | 1–500 IU |
| Thiamine | $0.1-10 \times 10^{-3}$ |
| Riboflavin | $0.1-10 \times 10^{-3}$ |
| Niacin | $2-20 \times 10^{-3}$ |
| Vitamin B6 | $0.1-20 \times 10^{-3}$ |
| Folic Acid | $50-1000 \times 10^{-6}$ |
| Vitamin B12 | $0.3-100 \times 10^{-6}$ |
| Biotin | $25-200,000 \times 10^{-6}$ |
| Pantothenic acid | $1-50 \times 10^{-3}$ |

The composition will contain about $100-500 \times 10^{-3}$ parts by weight of a vitamin blend containing the above vitamins in the relative amounts and/or proportions given. As noted herein, certain vitamins, e.g., β-Carotene, Vitamins C and E, also provide an antioxidant function.

Inclusion of enzymes in the comprehensive dietary supplement enhances the absorption and metabolism of nutrients and optimizes the beneficial effect of foods a β-Carotene β-Carotene nd dietary supplements. Human enzymes can be classified, based on composition, as either simple or conjugated. The simple enzymes depend for catalytic activity only on their structural conformation as proteins. The conjugated enzymes require non-protein moieties for optimal enzymatic performance. These structures, also known as co-factors, are either metal ions or complex organic molecules termed coenzymes. For many enzyme systems, both a metal ion and a coenzyme are required. In some metabolic systems, more than one metal ion and/or coenzyme is required. Co-factors and metal ions are generally stable to heat, whereas most enzyme proteins can undergo irreversible denaturation upon heating. The cofactor-dependent enzymes bind the metals and/or coenzymes with varying degrees of affinity. In many cases, the essential cofactor may be removed from the enzyme protein by dialysis, chromatography, or other fractionation methods. However, some coenzymes are covalently bound to the protein molecule. The intact enzyme-cofactor complex is called a holoenzyme. When the cofactor is removed, the remaining protein, which is partially or completely inactive, is called an apoenzyme. Many in vitro studies demonstrate that the reaction kinetics efficiency (RKE), in which a cofactor-dependent enzyme converts a substrate to a product, is dependent on the concentration of one or more co-factors present. Efficiency increases as the cofactor concentration increases. Furthermore, studies show that if a holoenzyme requires more than one cofactor, whether it be a metal ion or coenzyme, the effect on RKE is greatly enhanced when these multiple cofactors are present. Again, the efficiency increases as cofactor concentrations increase. Illustrative enzymes that require zinc as a cofactor include alcohol dehydrogenase, carbonic anhydrase, and carboxypeptidase. Enzymes that require magnesium as a cofactor include phosphohydrolases, pyruvate phosphokinase, plasma membrane ATPase, and phosphotransferases. Illustrative enzymes that require manganese as a cofactor include arginase and phosphotransferases. Enzymes that require iron ($Fe^{2+}$ or $Fe^{3+}$) include cytochromes, peroxidases, catalase, and ferredoxin. Enzymes that require copper ($Cu^{2+}$ or $Cu^{3+}$) as a cofactor include tyrosinase and cytochrome oxidase. Enzymes that require potassium as a cofactor include plasma membrane ATPase and pyruvate phosphokinase. An enzyme that requires sodium as a cofactor includes plasma membrane ATPase.

In such holoenzymes the metal ion may serve one of five possible roles. First, it may function as a bridging group to bind substrate and enzyme together through formation of a coordination complex. Secondly, it may serve as a catalytic group. For example, the iron atoms of catalase, which catalyzes decomposition of hydrogen peroxide, are believed to be its catalytic centers. Simple iron salts possess some capacity to decompose hydrogen peroxide, but this decomposition is greatly enhanced by the enzyme. Thirdly, it may function as a bridging group between neighboring amino acids, thereby generating or reinforcing an optimal three dimensional gross conformation of the enzyme. For example, dialysis studies show that as the efficiency of enzyme catalysis improves as a function of metal ion concentration, changes in the gross conformation of the protein are observed as measured by various methods including analytical centrifugation, intrinsic viscosity, optical rotatory dispersion, circular dichroism, and difference spectroscopy. Furthermore, it may alter the net surface charge of the enzyme, thereby increasing the half-life of the molecule and stabilizing it against the effects of enthalpy of ionization. In addition, it may help to induce a stabilized quaternary structure of the enzyme system.

Coenzymes usually function as intermediary carriers of electrons or of specific atoms or functional groups that are transferred in the overall enzymatic reaction. Some coenzymes are very tightly bound to the enzyme molecule. An example is the prosthetic heme group of cytochrome c, which is covalently bound to its peptide chain. In many cases, the coenzyme is only loosely bound and has some of the characteristics of the substrate. Many coenzymes contain certain trace substances as active components such as riboflavin, thiamine, pantothenic acid, and niacinamide. These are essential to the function of all cells. Illustrative coenzymes and the types of reactions in which they participate include:nicotinamide adenine dinucleotide, nicotinamide adenine dinucleotide phosphate, flavin mononucleotide, flavin adenine dinucleotide, and coenzyme Q for transfer of hydrogen atoms (electrons), thiamine pyrophosphate for transfer of aldehydes, coenzyme A and lipoamide for the transfer of acyl groups, cobamide coenzymes for transfer of alkyl groups, biocytin for transfer of carbon dioxide, pyridoxal phosphate for transfer of amino groups, and tetrahydrofolate coenzymes for transfer of methyl, methylene, formyl, or formimino groups.

An example of cofactor codependence can be illustrated with magnesium. Magnesium has been shown to activate alkaline phosphatases and pyrophosphatases isolated from mammalian tissue. Prostatic acid phosphatase also requires magnesium for optimal activity. Enzymes that catalyze the transfer of phosphate from ATP to a receptor or from a phosphorylated intermediate to ADP are activated by magnesium ions. These include hexokinase, fructokinase, creatinine transphosphorylase, phosphopyruvic transphosphorylase, phosphoglyceric transphosphorylase, acetyl-transphosphorylase, diphosphopyridine nucleotide phosphorylase, and phosphoglucomutase. Magnesium is also an activator for all enzymes that require the coenzyme thiamine phosphate. Carboxylases isolated from heart muscle are magnesium-requiring enzymes, such as the pyruvate oxidase system of the brain. Magnesium also serves as a cofactor for peptidases, such as leucine amino peptidase.

Enzymes can also be administered orally to yield a variety of beneficial health effects. For example, certain proteases have been found to redissolve fibrin deposits, reducing edema, and otherwise keeping the inflammatory responses of the body within bounds. I. Innerfield, Physiological and Clinical Effects of Buccally Given Proteases, 170 J. Am. Med. Ass'n 925–929 (1959). The mechanisms whereby proteases act in countering inflammation include: destroying or inactivating cell surface enzymes involved in the formation of eicosanoids (decrease proinflammatory eicosanoids, increase antiinflammatory eicosanoids); destroying or inactivating bradykinins (reduction in pain, prevention of progression of inflammation); reducing viscosity of extracellular fluid (increases nutrient and waste transport to and from injured sites, reduces edema); activating endogenous proteases (plasmin, prevents excess thrombin clot formation); inducing antiproteases (antiproteases mediate inflammation and inhibit progression of inflammation); substituting for endogenous proteases (activate endogenous systems), and bolstering molecular debridement (removal of necrotic tissue, and proteins, aids phagocyte functions, reduces edema). L. R. Bucci, Nutrition Applied to Injury Rehabilitation and Sports Medicine 167–176 (1992).

In addition to anti-inflammatory effects, proteases are administered orally for digestive enzyme replacement (digestive aids, cystic fibrosis) and for potentiation of drug effects, especially of antibiotics. Some of the more commonly used proteases in research studies, clinical practice, and in pharmaceutical agents include pancreatin, trypsin, chymotrypsin, bromelain, papain, chymopapain, fungal proteases, subtilins, ficins, and streptikinase-streptodornase. Id. Pancreatin possesses trypsin, chymotrypsin, carboxypeptidase, elastase, and other peptidase activities. Trypsin hydrolyzes peptide bonds, mostly at lysine and arginine residues. Chymotrypsin is specific for hydrolysis of peptide bonds around carboxyl groups. Bromelain is a group of enzymes with proteolytic and other activities isolated from pineapple stems and fruit. Bromelain exhibits broad spectrum lytic activity for peptide bonds. Papain and chymotrypsin are isolated from the latex of green papaya fruit and exhibit similar activities as bromelain. Fungal proteases are usually produced by fermentation of *Aspergillus oryzae*, and they exhibit broad spectrum peptide specificity. Subtilins are isolated from the fermentation of *Bacillus subtilis*. Subtilins have broad spectrum activity for peptide bonds. Ficin is isolated from the sap of certain fig trees. Ficin, chymopapain, and subtilins are not usually used for preparation of oral products.

The absorption of proteases after oral administration to animals and humans has been extensively studied by major pharmaceutical companies. The prevailing findings of most of these bioavailability studies is that proteases can be absorbed intact, with activity preserved, into circulation in measurable amounts. In general, the percentage of total protease activity absorbed into the circulation is from about 1 to 40%. Additional information on absorption of proteins can be found in M. Gardner, Gastrointestinal Absorption of Intact Proteins, 8 Ann. Rev. Nutrition 329–350 (1988); F. Klaschka, Oral Enzymes—New Approach to Cancer Treatment (Forum Medizin, 1996).

Therefore, it is advantageous to add blend of enzymes to the comprehensive dietary supplement:

| Enzymes | RANGES IN PARTS BY WEIGHT |
| --- | --- |
| Aspergillus enzymes | $0–230 \times 10^{-3}$ |
| Amylase | $0–230 \times 10^{-3}$ |
| Lipase | $0–230 \times 10^{-3}$ |
| Protease | $0–230 \times 10^{-3}$ |
| Cellulase | $0–230 \times 10^{-3}$ |

-continued

| Enzymes | RANGES IN PARTS BY WEIGHT |
|---|---|
| Bromelain | $0–230 \times 10^{-3}$ |
| Papain | $0–230 \times 10^{-3}$ |

The composition will contain about $30–500 \times 10^{-3}$ parts by weight of an enzyme blend containing one or more of the above enzymes in the relative amounts and/or proportions given All families of plant food are known to contain phytonutrients, which are unique substances produced during the natural course of plant growth and development and that are specific to each plan's genes and environment. The term phytonutrition refers to the role of these substances in supporting health in cultural food practices and cuisines worldwide. In addition to their phytonutritive role, phytonutrients have a phytotherapeutic role, acting as modifiers of physiological function. Grapeseed extract and soybeans, for example, contain high levels of four substances with proven anticancer activity: folic acids, glycosides, phytosterol and protease inhibitors. The consumption of 30–50 mg per day of soy isoflavones in traditional oriental populations and the ability of this diet to help lower the incidence of breast cancer among oriental women is an example of phytotherapeutic effect. It has been discovered that certain phytonutrients not only modify physiological function but are also useful to inhibit the effects and infectivity of the AIDS and other virues. Therefore, it is beneficial to add phytonutrients to the comprehensive dietary supplement:

| Blend of Phytonutrients | RANGES IN PARTS BY WEIGHT |
|---|---|
| Grape seed extract | $0–642 \times 10^{-3}$ |
| Lecithin | $0–642 \times 10^{-3}$ |
| Broccoli | $0–642 \times 10^{-3}$ |
| Cabbage | $0–642 \times 10^{-3}$ |
| Carrot | $0–642 \times 10^{-3}$ |
| Apple Pectin | $0–642 \times 10^{-3}$ |
| Atlantic Kelp | $0–642 \times 10^{-3}$ |
| Fructo-oligosaccharides (FOS) | $0–270 \times 10^{-3}$ |

The composition will contain about $250–750 \times 10^{-3}$ parts by weight of a phytonutrient blend containing one or more of the above phytonutrients in the relative amounts and/or proportions given It may be advantageous to assure the presence of certain specific antioxidants in the composition. β-carotene, vitamin E, selenium, and vitamin C are all known antioxidants, and are mentioned above as being contained in either the vitamin or mineral blends. Additionally, other known antioxidants, such as N-acetyl cysteine and lipoic acid, may be included. These particular substances provide a protective effect against free radical induced mutations of DNA and oxidative damage that can occur in the gastrointestinal system as well as in various target tissues and organs including the liver, lungs, kidneys, and blood. These ingredients may be added to the basic formulation in the following concentrations:

| ANTIOXIDANTS | RANGES IN PARTS BY WEIGHT |
|---|---|
| N-acetyl cysteine | $0–500 \times 10^{-3}$ |
| Lipoic acid | $0–200 \times 10^{-6}$ |

When present N-acetyl cysteine will be found in amounts ranging between about 50 and $500 \times 10^{-3}$ parts by weight and lipoic acid will be present in amounts ranging between about 20 and $200 \times 10^{-6}$ parts by weight.

In addition to the above-described ingredients, it may be advantageous to add certain lipotropic agents to increase the metabolism of fat in the body by hastening the removal or decreasing the deposit of fat in the liver. These ingredients include choline, inositol, pantetheine, and betaine hydrochloride. They may be added to the basic formulation, with or without other ingredients mentioned above, in the following amounts:

| LIPOTROPIC AGENTS | RANGES IN PARTS BY WEIGHT |
|---|---|
| Choline | $0–100 \times 10^{-3}$ |
| Inositol | $0–100 \times 10^{-3}$ |
| Pantetheine | $0–250 \times 10^{-3}$ |
| Betaine Hydrochloride | $0–100 \times 10^{-3}$ |

When present the composition will contain about $100–550 \times 10^{-3}$ in parts by weight of one or more of the above referenced lipotropic agents.

Many common dietary herbs have documented beneficial palliative effects.

Ginko biloba has been shown to increase circulation to the brain by increasing blood flow through the capillaries that are farthest from the heart, to enhance the brain's ability to metabolize glucose and increase nerve transmission. In addition, it has been shown that ginko biloba has many compounds with therapeutic benefits such as countering depression, senility and impotence. Siberian Ginseng, which contains the phytonutrient gineosie, has been used as health-promotion herb in oriental nutrition. Ginseng has been found to prevent carcinogen induced cancer in mice, it has also been found to protect against inflammation which is probably important in the nutritional prevention of cancer. Therefore, it is desirable to add certain beneficial herbs to the comprehensive dietary supplements:

| Herb Blend | RANGES IN PARTS BY WEIGHT OR BY UNIT |
|---|---|
| Gingko biloba | $0–180 \times 10^{-3}$ |
| Garlic | $0–180 \times 10^{-3}$ |
| Cayenne pepper | 40,000 H.U. |
| Green tea extract | $0–98.30 \times 10^{-3}$ |
| Gotu Kola extract | $0–98.30 \times 10^{-3}$ |
| Tumeric extract | $0–98.30 \times 10^{-3}$ |
| Siberian Ginseng | $0–98.30 \times 10^{-3}$ |
| Aloe vera extract | $0–98.30 \times 10^{-3}$ |

When present the composition will contain about $50–500 \times 10^{-3}$ of a blend one or more of the above herbs.

In addition, it may be advantageous to add certain other ingredients, such as amino acids, dietary fiber, buffering agents, formulation aids, diluents, excipients, colorants, and the like. These can be added in amounts as routinely used in the art. Typical of such ingredients include gelatin, cellulose, dicalcium phosphate, stearic acid, silicon dioxide, L-isoleucine, L-leucine, and L-valine.

The composition is preferably manufactured by agglomerating the raw materials in a suitable agglomerator so as to result in a finished product having a uniform composition with precise proportions of the components. The agglomerated material is then preferable packaged in capsules or other suitable dosage forms. Preferably, the capsules are to be taken with meals. The powdered composition may also be mixed with water, fruit juices, milk, or beverages for consumption. In some formulations, such as the formulation of Example 2, the maximum recommended dosage is 4 capsules per day. In other formulations, such as the formulation of Example 3, up to 12 capsules can be taken per day. Children younger than 4 years of age should not consume these dietary supplments. In addition, accidental overdose of iron-containing products can be fatal in children under 6 years of age. Thus, caution should be used in administering such formulations to young children.

The following formula represents specific embodiments of the invention. These may be prepared in the manner indicated above by blending together the stated raw material ingredients in an agglomerator so as to result in a finished product having a uniform composition with the precise proportions of the components as indicated. The agglomerated material is then packaged in a capsule.

EXAMPLE 1

Illustrative of a comprehensive dietary supplement composition comprising in parts by weight or, where applicable, in international units (IU) is as follows:

| | |
|---|---|
| Vitamin A | 500–20,000 IU |
| Vitamin C | 10–500 × $10^{-3}$ |
| Vitamin D | 25–1000 IU |
| Vitamin E | 1–500 IU |
| Thiamine | 0.1–10 × $10^{-3}$ |
| Riboflavin | 0.1–10 × $10^{-3}$ |
| Niacin | 2–20 × $10^{-3}$ |
| Vitamin B6 | 0.01–20 × $10^{-3}$ |
| Folic Acid | 50–1000 × $10^{-6}$ |
| Vitamin B12 | 0.3–100 × $10^{-6}$ |
| Biotin | 25–200,000 × $10^{-6}$ |
| Pantothenic acid | 1–50 × $10^{-3}$ |
| Calcium | 50–500 × $10^{-3}$ |
| Iron | 1–50 × $10^{-3}$ |
| Magnesium | 5–500 × $10^{-3}$ |
| Zinc | 1–25 × $10^{-3}$ |
| Selenium | 1–75 × $10^{-6}$ |
| Copper | 0.1–2 × $10^{-3}$ |
| Manganese | 0.1–10 × $10^{-3}$ |
| Chromium | 25–300 × $10^{-6}$ |
| Choline | 9 × $10^{-3}$ |
| Inositol | 15 × $10^{-3}$ |
| Boron | 0.025–25 × $10^{-3}$ |
| Vanadium | 0.1–10 × $10^{-6}$ |
| Phytonutrient Blend | 250–750 × $10^{-3}$ |
| Enzyme Blend | 30–500 × $10^{-3}$ |
| Herb Blend | 50–500 × $10^{-3}$ |

EXAMPLE 2

An illustrative specific embodiment of the present invention includes the following ingredients in parts by weight or, where applicable, in international units (IU):

| | |
|---|---|
| Vitamin A | 11,250 IU |
| Vitamin C | 284 × $10^{-3}$ |
| Vitamin D | 210 IU |
| Vitamin E | 200 IU |
| Thiamine | 6 × $10^{-3}$ |
| Riboflavin | 6 × $10^{-3}$ |
| Niacin | 15 × $10^{-3}$ |
| Vitamin B6 | 12 × $10^{-3}$ |
| Folic Acid | 200 × $10^{-6}$ |
| Vitamin B12 | 15 × $10^{-6}$ |
| Biotin | 150 × $10^{-6}$ |
| Pantothenic acid | 25 × $10^{-3}$ |
| Calcium | 200 × $10^{-3}$ |
| Iron | 6.75 × $10^{-3}$ |
| Iodine (KI) | 150 × $10^{-6}$ |
| Magnesium | 200 × $10^{-3}$ |
| Zinc | 7.5 × $10^{-3}$ |
| Selenium | 50 × $10^{-6}$ |
| Copper | 1 × $10^{-3}$ |
| Manganese | 5 × $10^{-3}$ |
| Chromium | 200 × $10^{-6}$ |
| Choline | 9 × $10^{-3}$ |
| Inositol | 15 × $10^{-3}$ |
| Boron | 50 × $10^{-6}$ |
| Vanadium | 3.75 × $10^{-6}$ |
| Blend of Phytonutrients | 642 × $10^{-3}$ |
| Grape seed extract | |
| Lecithin | |
| Broccoli | |
| Cabbage | |
| Carrot | |
| Apple Pectin | |
| Atlantic Kelp | |
| Enyme Blend | 230 × $10^{-3}$ |
| Aspergillus enzymes | |
| Amylase | |
| Lipase | |
| Protease | |
| Cellulase | |
| Bromelain | |
| Papain | |
| Herb Blend | 180 × $10^{-3}$ |
| Gingko biloba | |
| Garlic | |
| Cayenne pepper (40,000 H.U.) | |

EXAMPLE 3

Another illustrative specific embodiment of the present invention includes the following ingredients in parts by weight or, where applicable, in international units (IU):

| | |
|---|---|
| Vitamin A | 1,333 IU |
| β-Carotene | 3.333 × $10^{-6}$ |
| Vitamin C | 94.66 × $10^{-3}$ |
| Vitamin D | 70 IU |
| Vitamin E | 66.66 IU |
| Thiamine | 2 × $10^{-3}$ |
| Riboflavin | 2 × $10^{-3}$ |
| Niacin | 16.66 × $10^{-3}$ |
| Vitamin B6 | 4 × $10^{-3}$ |
| Folic Acid | 266.66 × $10^{-6}$ |
| Vitamin B12 | 60 × $10^{-6}$ |
| Biotin | 50 × $10^{-6}$ |
| Pantothenic acid | 8.33 × $10^{-3}$ |
| Calcium | 133.33 × $10^{-3}$ |
| Iron | 2.25 × $10^{-3}$ |
| Iodine (KI) | 50 × $10^{-6}$ |
| Magnesium | 133.33 × $10^{-3}$ |
| Zinc | 5 × $10^{-3}$ |
| Selenium | 16.66 × $10^{-6}$ |
| Copper | 0.33 × $10^{-3}$ |
| Manganese | 1.66 × $10^{-3}$ |
| Chromium | 66.66 × $10^{-6}$ |
| Molybenum | 10 × $10^{-6}$ |
| Potassium | 33 × $10^{-3}$ |
| Choline | 3 × $10^{-3}$ |
| Inositol | 5 × $10^{-3}$ |
| Boron | 16.66 × $10^{-6}$ |
| Vanadium | 1.25 × $10^{-6}$ |

-continued

| | |
|---|---|
| Blend of Amino Acids | 40.66 × $10^{-3}$ |
| L-isoleucine | |
| L-leucine | |
| L-valine | |
| Blend of Phytonutrients | 270 × $10^{-3}$ |
| Grape seed extract | |
| Broccoli | |
| Cabbage | |
| Carrot | |
| Apple Pectin | |
| Lecithin | |
| Fructo-oligosaccharides (FOS) | |
| Enzyme Blend | 36.66 × $10^{-3}$ |
| Aspergillus enzymes | |
| Amylase | |
| Bromelain | |
| Papain | |
| Herb Blend | 98.30 × $10^{-3}$ |
| Gingko biloba | |
| Green tea extract | |
| Gotu Kola extract | |
| Tumeric extract | |
| Siberian Ginseng | |
| Cayenne pepper (40,000 HU) | |
| Aloe vera extract | |

Additional modifications and improvements of the present invention may also by apparent to those skilled in the art. Thus, the particular combinations of parts described and illustrated herein is intended to represent only one embodiment of the invention, and is not intended to service limitations of alternative composition within the spirit and scope of the invention.

I claim:

1. A comprehensive dietary supplement composition comprising in parts by weight (a) about 100–500×$10^{-3}$ of a blend of vitamins, (b) about 200–800×$10^{-3}$ of blend of minerals, wherein said minerals are present as amino acid chelates formed from an amino acid ligand and said minerals, wherein the mole ratio of amino acid ligand to mineral in said chelate is at least 1:1 and wherein said chelate has a stability constant of between about $10^6$ and $10^{16}$, (c) about 250–750×$10^{-3}$ of a blend of phytonutrients, (d) about 50–500×$10^{-3}$ of a blend of herbs, and (e) about 30–500×$10^{-3}$ of a blend of enzymes.

2. The composition according to claim 1, wherein minerals are selected from the group consisting of calcium, iron, magnesium, zinc, selenium, copper, manganese and chromium.

3. The composition according to claim 2, wherein the mineral amino acid chelate has a ligand to mineral mole ratio of at least 2:1.

4. The composition according to claim 2, wherein the blend of the vitamins is selected from the group consisting of vitamin A, vitamin C, vitamin D, vitamin E, thiamine, riboflavin, niacin, vitamin B6, folic acid, vitamin B12, biotin, and pantothenic acid.

5. The composition according to claim 4, wherein the blend of the phytonutrients comprises at least one member selected from the group consisting of grape seed extract, lecithin, broccoli, cabbage, carrot, apple pectin, Atlantic kelp, or fructo-oligosaccharides, and mixtures thereof.

6. The composition according to claim 4, wherein the blend of herbs comprises at least one member selected from the group consisting of Ginkgo biloba, garlic, cayenne pepper, green tea extract, goto kola extract, tumeric extract, siberian ginseng, or Aloe vera extract, and mixtures thereof.

7. The composition according to claim 4, wherein the blend of enzymes comprises at least one member selected from the group consisting of Aspergillus enzymes, amylase, lipase, protease, cellulase, bromelain, or papain, and mixtures thereof.

8. The composition according to claim 4, wherein said composition is contained in one or more capsules which comprise a unit dosage.

9. The composition according to claim 8, wherein said composition is admixed in a carrier selected from the group consisting of gelatin, cellulose, dicalcium phosphate, stearic acid, or silicon dioxide, and mixtures thereof prior to being encapsulated.

10. The composition according to claim 4, further comprising about 100–550×$10^{-3}$ in parts by weight of a lipotropic agent selected from the group consisting of choline, inositol, pantetheine, or betaine hydrochloride, and mixtures thereof.

11. The composition according to claim 4, further comprising about 10–45×$10^{-3}$ in parts by weight of a branched amino acid selected from the group consisting of L-isoleucine, L-leucine, or L-valine, and mixtures thereof.

12. The composition according to claim 4, further comprising about 50 and 500×$10^{-3}$ parts by weight N-acetyl cysteine and about 20 and 200×$10^{-6}$ parts by weight lipoic acid.

13. The composition according to claim 4, further comprising about 0.0250–25×$10^{-3}$ parts by weight boron and about 0.1–10×$10^{-6}$ parts by weight vanadium.

14. A method for ameliorating effects of stress and premature aging, for enhancing cellular rejuvenation and regeneration, and for fortifying the immune system of a warmblooded animal or human, comprising administrating to said human or animal a dietary supplement composition comprising in parts by weight (a) about 100–500×$10^{-3}$ of a blend of vitamins, (b) about 200–800×$10^{-3}$ of blend of minerals, wherein said minerals are present as amino acid chelates formed from an amino acid ligand and said minerals, wherein the mole ratio of amino acid ligand to mineral in said chelate is at least 1:1 and wherein said chelate has a stability constant of between about $10^6$ and $10^{16}$, (c) about 250–750×$10^{-3}$ of a blend of phytonutrients, (d) about 50–500×$10^{-3}$ of a blend of herbs, and (e) about 30–500×$10^{-3}$ of a blend of enzymes.

15. The method according to claim 14, wherein the minerals are selected from the group consisting of calcium, iron, magnesium, zinc, selenium, copper, manganese and chromium.

16. The method according to claim 15, wherein the mineral amino acid chelate has a ligand to mineral mole ratio of at least 2:1.

17. The method according to claim 15, wherein the vitamins are selected from the group consisting of vitamin A, vitamin C, vitamin D, vitamin E, thiamine, riboflavin, niacin, vitamin B6, folic Acid, vitamin B12, biotin, and pantothenic acid.

18. The method according to claim 17, wherein the blend of phytonutrients comprises at least one member selected from the group consisting of grape seed extract, lecithin, broccoli, cabbage, carrot, apple pectin, Atlantic kelp, fructo-oligosaccharides, and mixtures thereof.

19. The method according to claim 17, wherein the blend of herbs comprisies at least one member selected from the group consisting of Ginkgo biloba, garlic, cayenne pepper, green tea extract, goto kola extract, tumeric extract, siberian ginseng, Aloe vera extract, and mixtures thereof.

20. The method according to claim 17, wherein the blend of enzymes comprises at least one member selected from the group consisting of Aspergillus enzymes, amylase, lipase, protease, cellulase, bromelain, papain, and mixtures thereof.

21. The method according to claim 17, wherein said composition is contained in one or more capsules which comprise a unit dosage.

22. The method according to claim 17, wherein said composition is admixed in a carrier selected from the group consisting of gelatin, cellulose, dicalcium phosphate, stearic acid, or silicon dioxide, and mixtures thereof prior to being encapsulated.

23. The method according to claim 17, wherein the composition further comprises about $100\text{--}550 \times 10^{-3}$ in parts by weight of a lipotropic agent selected from the group consisting of choline, inositol, pantetheine, and betaine hydrochloride, and mixtures thereof.

24. The method according to claim 17, wherein the composition further comprising about $1045 \times 10^{-3}$ in parts by weight of a branched amino acid selected from the group consisting of L-isoleucine, L-leucine, L-valine, and mixtures thereof.

* * * * *